(12) United States Patent
Oshiumi et al.

(10) Patent No.: US 7,062,080 B2
(45) Date of Patent: Jun. 13, 2006

(54) METHOD OF INSPECTING CURVED SURFACE AND DEVICE FOR INSPECTING PRINTED CIRCUIT BOARD

(75) Inventors: Akira Oshiumi, Kyoto (JP); Yoshiki Fujii, Kyoto (JP); Yujin Fujita, Tagata-gun (JP)

(73) Assignee: Omron Corporation, Kyoto (JP)

( * ) Notice: Subject to any disclaimer, the term of this patent is extended or adjusted under 35 U.S.C. 154(b) by 688 days.

(21) Appl. No.: 10/299,570

(22) Filed: Nov. 18, 2002

(65) Prior Publication Data

US 2003/0099393 A1 May 29, 2003

(30) Foreign Application Priority Data

Nov. 26, 2001 (JP) .............................. 2001-360014
Nov. 26, 2001 (JP) .............................. 2001-360015

(51) Int. Cl.
*G06K 9/00* (2006.01)
(52) U.S. Cl. ...................... 382/141; 382/144; 382/145; 382/146; 382/147
(58) Field of Classification Search ........ 382/141–152; 348/83, 92–95, 125–132, 134
See application file for complete search history.

(56) References Cited

U.S. PATENT DOCUMENTS

| 5,039,868 | A | | 8/1991 | Kobayashi et al. | .......... 250/572 |
|---|---|---|---|---|---|
| 5,093,797 | A | * | 3/1992 | Yotsuya et al. | ................ 716/16 |
| 6,023,663 | A | * | 2/2000 | Kim | ............................. 702/81 |
| 6,246,788 | B1 | | 6/2001 | Pattikonda et al. | .......... 382/147 |
| 6,396,949 | B1 | * | 5/2002 | Nichani | ........................ 382/173 |
| 6,687,396 | B1 | * | 2/2004 | Sugiura et al. | ............. 382/141 |
| 6,874,420 | B1 | * | 4/2005 | Lewis et al. | ................. 101/485 |
| 6,947,151 | B1 | * | 9/2005 | Fujii et al. | ................... 356/612 |

FOREIGN PATENT DOCUMENTS

| EP | 0231941 | 8/1987 |
|---|---|---|
| EP | 0452905 | 10/1991 |
| EP | 0685732 | 12/1995 |
| EP | 1116950 | 7/2001 |
| JP | 01-282410 | 11/1989 |
| JP | 02/300862 | 12/1990 |
| JP | 06/001173 | 1/1994 |
| JP | 06-339017 | 12/1994 |
| JP | 06/339017 | 12/1994 |

OTHER PUBLICATIONS

Solomon, F. et al. "Inspecting specular lobe objects using four light sources", I.E.E.E. Robotics and Automation, May 12-14, 1992. pp. 1707-1712 vol. 2.*
Patent Abstract of Japan vol. 1998, No. 4.

* cited by examiner

*Primary Examiner*—Samir Ahmed
*Assistant Examiner*—Brian Le
(74) *Attorney, Agent, or Firm*—Beyer Weaver & Thomas LLP (57) ABSTRACT

A circuit board with lead-free solder is inspected by using light sources with different colors at different angles to obtain an image having a plurality of color components. For each pixel within an area in the obtained image, the brightness of a white component generated by mixing all of the color components is extracted. The brightness of each of the color components of each pixel is reduced by an amount corresponding to the extracted brightness of the white component and is adjusted such that the brightest of the color components becomes more strongly emphasized compared to the others, than the brightness before the brightness-reducing process was carried out and the loss in total brightness caused by the brightness-reducing process is restored. The image with restored brightness is displayed and the surface condition of the solder is judged on the basis of the distributions of the color components of this image.

12 Claims, 6 Drawing Sheets

METHOD OF INSPECTING CURVED SURFACE AND DEVICE FOR INSPECTING PRINTED CIRCUIT BOARD

BACKGROUND OF THE INVENTION

This invention is in the technical field of inspecting a curved surface of an object such as a soldered part on a printed circuit board.

Figure 9:
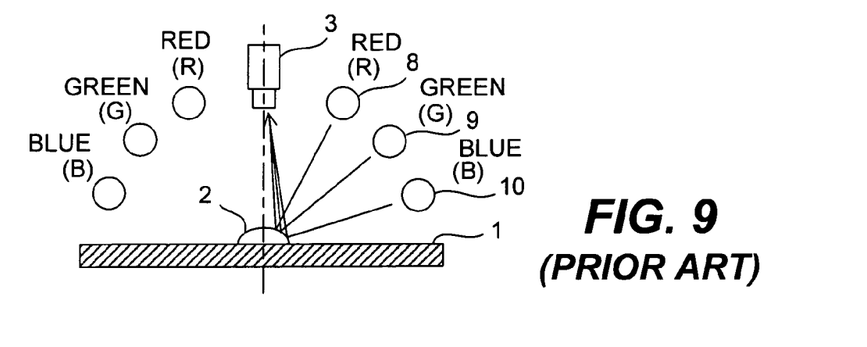
FIG. 9 is a schematic drawing for showing the structure of the optical system for the inspection device.
Figure 10:
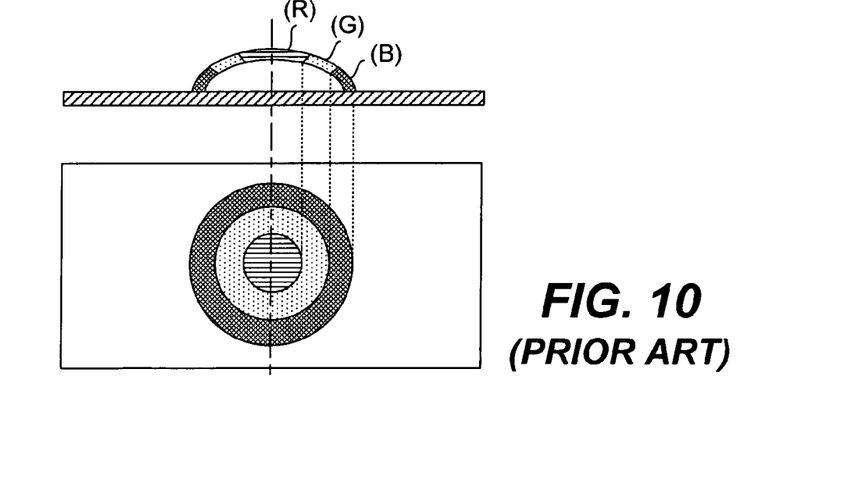
FIG. 10 is a schematic drawing for showing the principle of measurement by the optical system.

Japanese Patent Publication Tokko 6-1173 describes a device for automatically inspecting a soldered part on a printed circuit board by a method of image processing by making use of the mirror reflection from the solder part. As shown in FIG. 9, this device serves to form an image of a target object to be inspected by means of three light sources 8, 9 and 10 emitting respectively red (R), green (G) and blue (B) light and an image pick-up device 3. Each of the light sources 8, 9 and 10 is disposed obliquely above the solder 2 to be inspected. With a device thus structured, each of the colored light beams from the sources 8, 9 and 10 makes incidence on the solder 2 at a different position corresponding to the angular orientation of its source. If the solder surface is sloped so as to be able to lead the mirror-reflected beam therefrom to the image pick-up device 3, a two-dimensional image is formed as shown in FIG. 10 with the colors R, G and B separated, corresponding to the positions of incidence of the beams.

Figure 11:
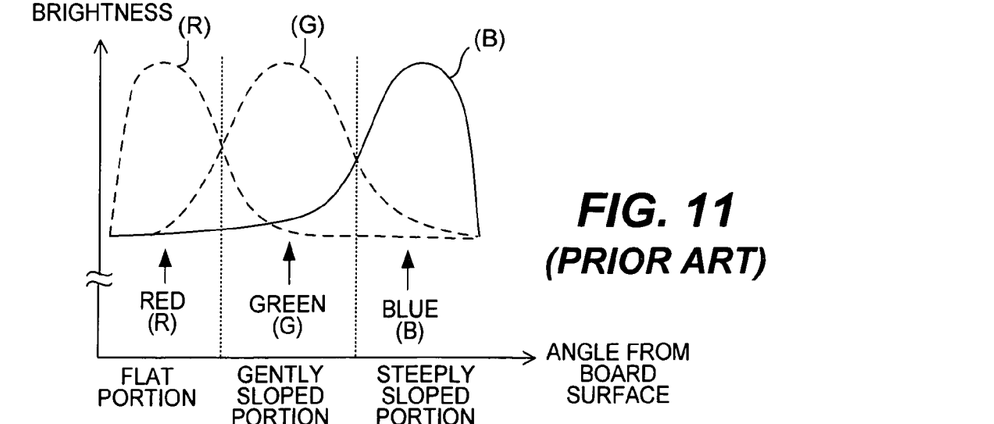
FIG. 11 is a graph for showing the brightness characteristic of an image of solder obtained by the optical system.

In the example shown in FIG. 9, the three light sources 8, 9 and 10 are arranged such that the angles of their orientation measured from the horizontal plane increase in the order of R, G and B, and these angles are determined according to the portions of the curved surface to be separately detected. Thus, if a dominant color is extracted at each point on the image obtained by the irradiation from the sources 8, 9 and 10, each color component can be clearly distinguishable as shown in FIG. 11, corresponding to a flat surface portion where the surface is nearly flat and the sloping is the smallest, a steeply sloped surface portion where the surface is the steepest, and a gently sloped surface portion in between.

Since a two-dimensional image can thus be obtained with each of the colors R, G and B separated according to the sloping angle of the solder surface, it is possible to determined the quality of the surface condition by preliminarily registering the pattern of each color on an image of a desired solder surface shape and comparing the color patterns on an image obtained from a target object of inspection.

Recently, however, lead-free solder is coming to be used more frequently by the makers of circuit boards in view of environmental problems. Since lead-free solder is a non-eutectic alloy with constituent metals having very different solidification temperatures, small protrusions and indentations are likely to be developed on its surface. As a result, lead-free solder has a higher diffusive reflectivity than conventional eutectic solder with lead and tin as principal constituents. Moreover, the brightness of each light source is usually adjusted, for the ease of visual inspection by the operator, such that a white color will result if the diffused light from each source is mixed together. Thus, if an image is formed of an object with a high diffusive reflectivity such as lead-free solder, the image as a whole becomes white as each color component is mixed together or the boundaries between color patterns become unclear and obscure. When the aforementioned adjustment is made, furthermore, a white-colored diffusive reflecting plate is disposed with its planar surface horizontally oriented and an image of its diffusive reflecting surface is obtained such that the operator can make adjustments while referencing the color of the diffusive reflecting surface on the image. Thus, the red color on the flat solder surface portion close to the disposed diffusive reflecting plate becomes particularly difficult to recognize visually.

At the time of teaching operation with the inspection device, an image of a model soldered part is displayed and the operator is required to set a threshold value for binary conversion for extracting each color pattern and a judgment reference value to be used for judging whether or not an extracted color pattern is acceptable or not. If a whitish image is generated because the color components are mixed together or if the boundaries between the color patterns become unclear, however, it is not easy and may take a long time to visually determine an appropriate threshold value for binary conversion. This optical system may be used for a visual inspection device, but it takes a long time to evaluate the condition of each target area to be inspected if it becomes difficult to ascertain subtle color differences at boundary areas between different color patterns.

If the diffusive reflectivity of the lead-free solder to be inspected increases, furthermore, the difference in brightness gradation of the color components becomes smaller, making it difficult to maintain a high level of accuracy in the inspection.

SUMMARY OF THE INVENTION

It is therefore an object of this invention to carry out a reliable inspection even on a curved surface of a target object having a high diffusive reflectivity such as lead-free solder.

A method embodying this invention for inspecting surface conditions of an object with a curved surface placed on a reference plane may be characterized as comprising the steps of obtaining an image from reflected light from the curved surface irradiated by a light including a plurality of color components having different colors projected from different directions with respect to the reference plane, carrying out, within an image area in the obtained image, an extracting process (or the "whiteness-extracting process" or the "whiteness-removing process") by extracting from each pixel the brightness of a white component generated by mixing all of the color components and a brightness-reducing process by reducing the brightness of each of the color components of each pixel by an amount corresponding to the extracted brightness of the white component of the pixel, carrying out, for each pixel of the image area for which the brightness-reducing process has been carried out, a brightness-restoring process by varying the brightness of each of the color components such that the brightest of the color components becomes more strongly emphasized compared to the others than before the brightness-reducing process was carried out and the loss in total brightness caused by the brightness-reducing process is at least partially restored, and carrying out an inspection of surface conditions of the curved surface based on distributions of the color components in the image after the brightness-restoring process was carried out. In the above, the reference plane may be the surface of a printed circuit board and the curved surface may be a surface portion of solder on the circuit board. The colors of the light projected from different directions may preferably be the three primary colors but light of a different set of colors may be used. In general, color images for display are formed with red (R), green (G) and blue (B) beams of light and a white color will result if these colors are mixed at equal proportions. Color components to be subjected to the brightness-reducing and brightness-restoring processes may be thought to be the light of different colors projected from different directions. Thus, when light beams of the three primary colors R, G and B are made incident on the curved surface, the color components to be processed are R, G and B.

The brightness (or intensity) of each color component corresponds to that of the reflected light received by the image pick-up device such as a camera. In the case of a digital image, the brightness may be expressed for each pixel. When brightness is expressed by gradation, it is preferable to increase the gradation number as the brightness is increased.

The aforementioned whiteness-extracting, brightness-reducing and brightness-restoring processes may each be carried out for each pixel within an image area including the image of the target object being inspected. Any specified quantity of brightness common to all color components in a digital variable-density image area including the image of the target object may be extracted as the white component. The brightness of the color component with the weakest brightness may be selected as the white component or a specified percentage of this brightness.

In the brightness-reducing process, the quantity of brightness extracted as that of the white component is subtracted from each color component. Since the white component generated by mixing the diffused reflected light of each color is thereby removed, the brightness of each color component after the brightness-reducing process reflects accurately the brightness of the mirror-reflection of each color from the target object.

In the brightness-restoring process, the brightness of the color component which became the brightest after the brightness-reducing process is made greater than that before the brightness-reducing process and the brightness of each color component is adjusted such that the loss in the total brightness caused by the brightness-reducing process will be restored to a value close to the total brightness before the brightness-reducing process. This may be done by calculating the ratio at which the total brightness of the color components was reduced and the brightness of each color component may be increased according to this ratio (a multiplicative factor). Alternatively, the brightness removed by the brightness-reducing process may be appropriately distributed among and added to the color components.

In this brightness-restoring process, it is desirable to restore the total brightness back to the original total brightness before the brightness-reducing process because there will be little difference in the total difference compared to the surrounding areas not being processed and there will be no strange sensation on the part of the operator watching the image for the teaching and inspection purposes. As long as the brightness is sufficient for visually ascertaining the distribution of each color, however, the total brightness may be lower than the level before the brightness-reducing process.

With the brightness-reducing and whiteness-extracting processes, an image with the colors distributed in the way corresponding to the brightness of the mirror-reflected light can be obtained. Since the darkened image is restored to the earlier level of total brightness by the brightness-restoring process and corrections are made such that the color component corresponding to the sloping angle of the curved target surface is emphasized, a sufficiently large difference can be generated between the most dominant component and the other components.

A method according to another embodiment of the invention may be characterized as comprising the steps of obtaining a reference image (the "first image") of a diffusive reflecting surface at a selected angle with respect to the reference plane under a condition of illumination by light with a plurality of color components having different colors projected from different directions with respect to the reference plane, determining multiplicative factors by which brightness of each of the color components of the first image is individually adjusted such that the color component corresponding to light from an angle corresponding to the selected angle becomes brighter than the other color components, obtaining an inspection image of reflected light (the "second image") from the curved surface to be inspected under the same condition as the condition of illumination under which the first image of the diffusive reflecting surface was obtained, carrying out an adjustment process by adjusting the brightness of each of the color components, within an area of the second image containing an image of the object, by the multiplicative factors, carrying out a whiteness-extracting process by extracting, from each pixel of the area after the adjustment process, the brightness of the white component generated by mixing all of the different colors and a brightness-reducing process by reducing the brightness of the color components, for each pixel, by an amount corresponding to the brightness of the white component extracted in the whiteness-extracting process, carrying out, for each pixel of the area for which the brightness-reducing process has been carried out, a brightness-restoring process by varying the brightness of each color component such that the brightest of the color components becomes more strongly emphasized with respect to the others of the color components than before the brightness-reducing process and the loss in total brightness caused by the brightness-reducing process is restored, and carrying out an inspection of surface conditions of the curved surface based on a distribution of the color components in the image after the brightness-restoring process.

In the above, "the light from an angle corresponding to the selected angle" means the light from the source disposed at the angle from which the surface with this selected angle can be observed. In other words, this is the light from the source disposed such that the mirror-reflected light can be led to the image pick-up device if the diffusive reflecting surface is replaced by a mirror surface having the same orientation. With reference to FIG. 9, if the diffusive reflecting surface is set at an angle corresponding to the flat portion of the solder, for example, it will be red light. If the sloping angle is set corresponding to the gently sloped surface portion of solder, it will be green light. If the sloping angle is set corresponding to the steeply sloped surface portion, it will be blue light.

The aforementioned steps of obtaining the first image and determining the multiplicative factors are steps to be carried out prior to the inspection. They are preferably repeated several times by changing the angle of the diffusive reflecting surface. For example, this angle is set sequentially according to the sloping angle of the surface to be detected by each of the color components and images are obtained under conditions of illumination with different color light. The multiplicative factors are determined such that on each of the obtained images the color component corresponding to the sloping angle of the diffusive reflecting surface will become brighter than the other color components. Thereafter the results of adjustment at each sloping angle is summarized to finally determine the multiplicative factors.

The step of obtaining the image of the target object to be inspected and the subsequent steps are to be carried out at the time of actual inspection. Thus, at the time of the actual inspection, an image is obtained of the reflected light from the target object and the brightness of each color component of the image of the target object is adjusted on the basis of the multiplicative factors and then the whiteness-extracting, brightness-reducing and brightness-restoring steps are sequentially carried out and the image thus processed is used to judge the surface conditions of the target object.

By this method, each image of a sloped surface corresponding to the direction of a light source is adjusted such that the color component which would be dominant if the sloped surface were a mirror surface will be emphasized. Thus, even if the curved surface of the target object has a high diffusive reflectivitly and the differences in brightness among the color components are difficult to observe, the a color distribution according to the sloping angle can be obtained. Since the whiteness-extracting, brightness-reducing and brightness restoring processes are carried out thereafter, the effects of diffusive reflected light can be eliminated and images with a clear color distribution can be obtained.

The aforementioned step of determining the multiplicative factors need not be carried out by using a diffusive reflecting plate. Alternatively, an image may be obtained of a model object with a known surface shape and the multiplicative factors may be determined such that patterns of sloped surfaces corresponding to the light sources on these images will appear as color patterns corresponding to these light sources.

The adjustment of these multiplicative factors may be effected not only on the brightness of the color components on the digital image but also on analog image signals. For example, as an analog image from the image pick-up device is transmitted to an image processor to have the gain adjusted, the gain of the image may be adjusted by the image processor. Alternatively, the output gain of the image pick-up device may be adjusted. When the gain of an image signal is adjusted, it is preferable to make the adjustment such that the color component corresponding to each sloping angle will become brighter than the other color components while the angle of the diffusive surface is sequentially changed according to the direction of each color.

When the brightness of a color component is adjusted, it is possible to make the adjustment only in the image area corresponding to the image of the curved surface to be inspected. When an analog image signal is adjusted, even image areas of no interest such as the portions corresponding to the upper surface of the circuit board or a component mounted thereon may also be adjusted. Since adjustments are made only so as to emphasize the color component corresponding to the sloping angle of the surface, there is hardly any trouble in visually ascertaining the image display as long as it is known what color is going to appear, depending on the sloping angle.

When the conditions of a curved surface is inspected by these inspection methods, the manner of distribution of each color in an image area including the image of the target surface to be inspected after the brightness-restoring process may be compared with preliminarily prepared model data for judging whether the surface being inspected is defective or not. Such model data may be obtained by obtaining an image of the curved surface of a model under the same conditions of illumination and image pick-up and then carrying out the whiteness-extracting, brightness-reducing and brightness restoring processes on the obtained image (as well as preliminarily adjusting the color components on the basis of the multiplicative factors if the second of the aforementioned methods is used).

It is desirable to form the aforementioned model data as a plurality of color patterns in the form of binary data obtained by using a threshold value ("binary threshold value") for each color component of the image of the curved target surface to be inspected. By this method, the image area including the image of the target curved surface to be inspected is converted into binary data by using the same threshold value and characteristics such as area and the position of the center of gravity of each color pattern may be compared with the corresponding characteristics on the model data. If the difference in such a comparison is found to be less than an allowable range, the surface condition of the target object may be considered to be not defective. The threshold for converting into binary representation and the characteristics of the model data to serve as standard values for the comparison may preferably be stored in a memory device.

With the methods described above, even the conditions of a diffusively reflecting surface can be automatically inspected with a high accuracy. When the condition of a curved surface is inspected visually by an operator, the inspection method may include the steps of displaying the image after the brightness-restoring process and receiving the data item indicating the operator's judgment. By such a displaying step, the operator can clearly see the distribution conditions of the color components at different sloping angles and hence an accurate judgment can be rendered.

A device for inspecting a printed circuit board according to this invention may be characterized as comprising a light projecting device having a plurality of light sources to emitting light of different colors, arranged at different angles with respect to a reference surface, an image pick-up device for generating an image from reflected light from the printed circuit board, an image inputting device for receiving the image generated by the image pick-up device with each of the light sources lit, whiteness-removing means for carrying out a whiteness-extracting process by extracting, from each pixel of an area of the image inputted by the image inputting device and containing an image of solder, the brightness of the white component generated by mixing all of the different colors and a brightness-reducing process by reducing the brightness of the color components, for each pixel, by an amount corresponding to the brightness of the white component extracted in whiteness-extracting process, brightness-restoring means for carrying out, for each pixel of the area for which the brightness-reducing process has been carried out, a brightness-restoring process by varying the brightness of each color component such that the brightest of the color components becomes more emphasized with respect to the others of the color components than before the brightness-reducing process and the loss in total brightness caused by the brightness-reducing process is restored, judging means for judging surface conditions of the solder by comparing preliminarily set model data with distribution of each of the colors in the area of the image after the brightness-restoring process, and an output device for outputting results of judgment by the judging means.

The light projecting device may include ring-shaped light sources for different colors such as red, green and blue but light sources emitting light of not any of the three primary colors or a source for white light may be included. The image pick-up device may be a CCD camera capable of generating image signals for the individual color components. The image signals generated by the image pick-up device need not be analog signals. The image pick-up device may be a digital camera.

The image inputting device is installed inside the apparatus for carrying out the image processing for the inspection and serves to generate an image to be processed. It may be comprised of an amplifier circuit for amplifying the image signals from the image pick-up device and an A/D converter for generating a digital image to be processed. If the image pick-up device is a digital camera, for example, the image inputting device may be in the form of an input port for individually receiving digital image data for different colors.

The whiteness-removing, brightness-restoring and judging means are each a control unit and preferably comprised of a CPU for carrying out a corresponding processing program. Parts of these means may be formed by a dedicated component such as an ASIC.

The output device may be formed as an interface for outputting the result of judgment by the judging means to external devices. A display device for displaying the result of judgment and a data memory means for causing the result of judgment to be stored in a memory medium may be included in the output device.

The whiteness-removing means serves to carry out the whiteness-extracting and brightness-reducing processes to convert the inputted image by removing the effects of the diffusive reflection from the surface of the solder to be inspected. The brightness-restoring means serves to carry out the brightness-restoring process such that the brightness of the image, lost in the brightness-reducing process, is recovered such that the most dominant color component will be emphasized.

The judging means serves to extract the individual color patterns in the image of the solder in the image after the brightness-restoring process and to compare these color patterns with model data for determining whether or not the surface conditions of the solder are defective. As explained above, the comparison may be made by way of characteristic quantities in the color patterns and the model data. For the purpose of this judging process, the inspection device is preferably provided with a memory for registering a threshold value for binary conversion (the binary threshold value) and judgment reference values according to the characteristic quantities associated with the model data. Model data themselves need not be registered in the memory device because if these characteristic values of the model data are registered, it may be considered that the model data have been registered.

It is also desirable that the inspection device be provided with a display device for displaying an image for the purpose of teaching and an input device such as a mouse, a keyboard and a consol.

With the inspection device of this invention, the processes by the whiteness-removing and brightness-restoring means are carried out also on the image picked up at the time of teaching and inputted and the processed image is displayed on the display device. Thus, the operator can easily select a position on the displayed image suited for the binary threshold value and the judgment reference value, and the processes of setting data for the inspection and registering them can be carried out efficiently.

Another device for inspecting a printed circuit board according to a second embodiment of this invention may be characterized as comprising a light projecting device, an image inputting device, whiteness-removing means, and brightness-restoring means, as described above for the device according to the first embodiment of the invention, as well as a display device for displaying an image after the brightness-restoring process and an input device for allowing the operator to input an data item indicative of the judgment result of an inspection based on the image of the solder displayed on the display device. This display device may include an device such as a CRT and LCD, a D/A conversion circuit and on interface for displaying the processed image. The input device, like that of the inspection device according to the first embodiment of the invention, may include a mouse, a keyboard and a consol, and the data inputted through the input device can be outputted to external devices and stored in a specified memory medium.

Since the image of the solder to be inspected after the whiteness-removing and brightness-restoring processes can be displayed on the display device, an accurate visual inspection is possible based on the color distribution made clearer according to the slope of the solder surface.

An inspection device according to either embodiment of the invention described above may be further provided with a brightness-adjusting means for carrying out the adjusting process (or the "brightness-adjusting process") by adjusting the brightness of each of the color components, within an area containing an image of the solder, by using predetermined multiplicative factors such that the whiteness-removing means may carry out the whiteness-extracting process on an image obtained by the brightness-adjusting process by the brightness-adjusting means. This brightness-adjusting means may be realized by the same computer in which the programs for the aforementioned whiteness-extracting and brightness-restoring processes are installed by installing also the program for its execution. Alternatively the brightness-adjusting means may be realized as means for adjusting the gain by being taken into the output gain from the image pick-up device or the image inputting device.

The multiplicative factors used for the adjustment of brightness of each color component are determined for each of the color components such that, when a reference image of a diffusive reflecting surface at an arbitrary angle with respect to the reference surface is obtained by the image pick-up device while the light sources are lit, the color component corresponding to the light at the angle corresponding to a specified angle becomes brighter than the others of the color components.

With such brightness-adjusting means, the image of the solder to be inspected is adjusted before the whiteness-extracting and brightness-restoring processes such that the color component corresponding to the sloping angle of the solder surface is emphasized. When the surface of lead-free solder with diffusive reflectivity is inspected, a color distribution according to the slope of the surface is obtained and then the effects of diffusively reflected light are removed such that the color distribution can be made clearer.

DETAILED DESCRIPTION OF THE INVENTION

Figure 1:
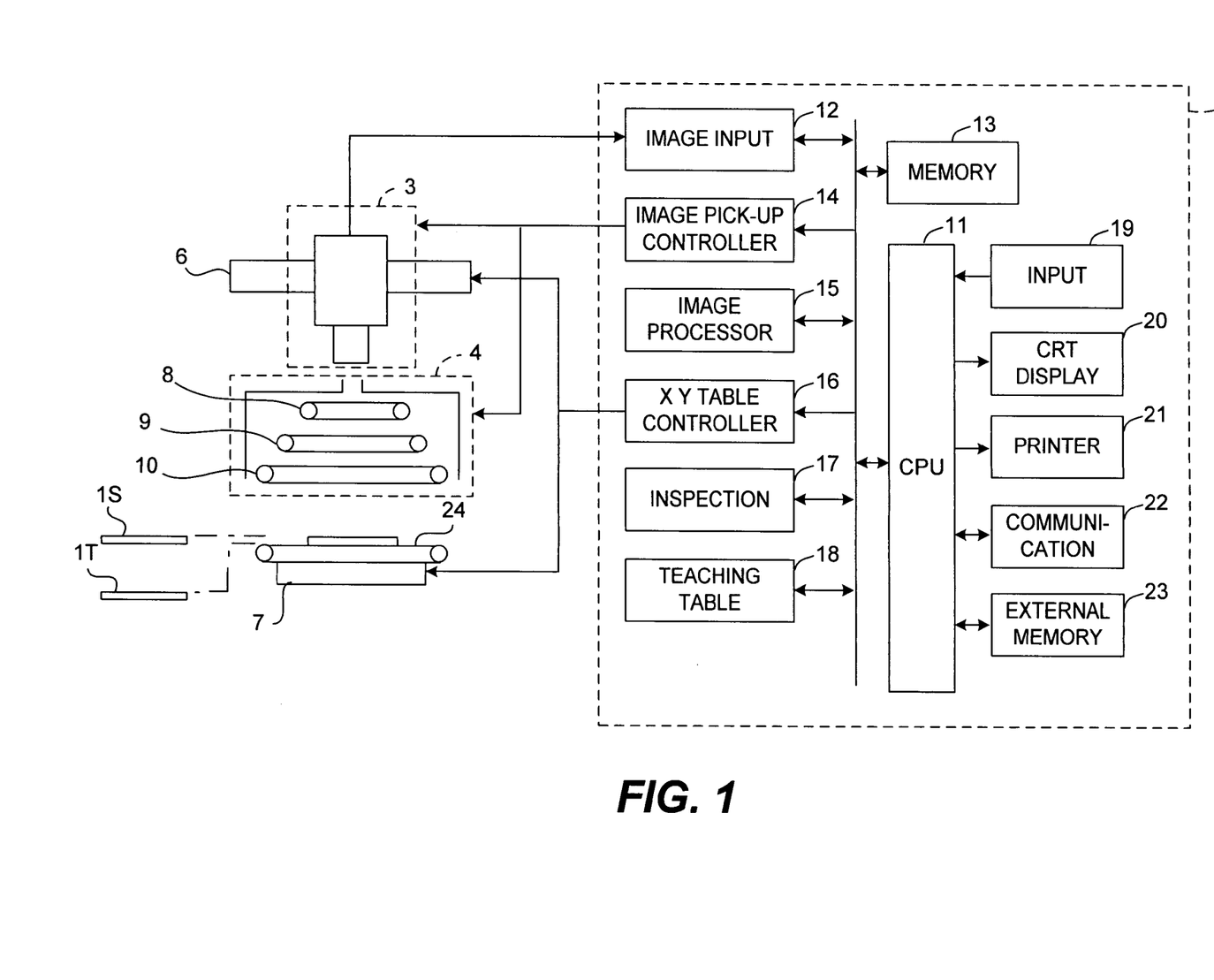
FIG. 1 is a block diagram of an inspection device embodying this invention for inspecting a printed circuit board.

The invention is described next by way of an example of a device for inspecting a printed circuit board with lead-free solder by obtaining an image of the circuit board and to process the image thus obtained, thereby determining the quality of soldered parts thereon. As shown in FIG. 1, the device comprises an image pick-up device 3, a light projecting device 4, a control unit 5, an X-table 6 and a Y-table 7. In FIG. 1, the target circuit board to be inspected is indicated by symbol 1T and a standard printed circuit board with properly soldered parts indicated by symbol 1S.

The Y-table 7 is provided with a conveyer 24 for supporting the circuit board 1S or 1T and adapted to be moved by a motor (not shown) to transport the circuit board 1S or 1T in the Y-direction (perpendicular to the plane of the page). The X-table 6 supports the image pick-up device 3 and the light projecting device 4 to move them in the X-direction (the left-right direction on the page) above the Y-table 7.

The light projecting device 4 comprises three annular light sources 8, 9 and 10 having different radii for emitting beams of red (R), green (G) and blue (B) light, respectively. They are all centered exactly above the point of observation and positioned at different angles from the support plane of the circuit board 1S or 1T.

The image pick-up device 3 may consist of a CCD camera for generating a color image with its optical axis oriented so as to pass through the centers of the three light sources 8, 9 and 10 in the perpendicular direction. Thus, the reflected light from the circuit board 1S or 1T enters the image pick-up device 3 and is converted into color signals R, G and B to be inputted to the control unit 5.

The control unit 5 may comprise a computer with a CPU 11 and may include an image input device 12, a memory device 13, an image pick-up controller 14, an image processor 15, an X-Y table controller 16, an inspection unit 17, a teaching table 18, an input device 19, a CRT display device 20, a printer 21, a communication (transmission-reception) device 22 and an external memory device 23.

The image input device 12 includes amplifier circuits for amplifying each of the image signals R, G and B from the image pick-up device 3 as well as an A/D converter for converting these image signals into digital signals. The memory device 13 stores variable-density image data on these digital quantities for the individual colors as well as binary image data obtained by converting such variable-density images into a binary form. The memory device 13 also stores multiplicative adjustment factors for the brightness of each color for the intensity adjustment process, to be described below.

The image pickup controller 14 is provided with an interface for connecting the image pick-up device 3 and the light projecting device 4 to the CPU 11 and serves to adjust the quantity of light from each light source of the light projecting device 4 on the basis of commands from the CPU 11 and to balance the outputted light of each color from the image pick-up device 3.

The X-Y table controller 16 includes an interface for connecting the X-table 6 and the Y-table with the CPU 11 and serves to control the movements of the X-table 6 and the Y-table 7 on the basis of commands from the CPU 11.

The teaching table 18 is a memory device for storing inspection data for each circuit board. For each circuit board, a judgment file including inspection data such as its set position and the size of the inspection area, "binary threshold values" (the threshold values for conversion into binary representation) necessary for extracting each of R, G and B color patterns within this inspection area (including not only binary threshold values for the individual color components but also binary threshold values related to brightness), reference values for making a judgment between "defective" and "not defective" by the extracted color patterns (set for quantity of each of characteristics such as pattern position and size) are stored in the teaching table 18. These judgment files are introduced by an operator prior to an inspection work by using an image obtained from the standard circuit board 1S. At the time of an inspection, they are read by the CPU 11 and sent in the memory device 13 to be supplied to the image processor 15 and the inspection unit 17.

The image processor 15 extracts from the image data R, G and B stored in the memory device 13 the individual brightness of R, G and B as well as the total brightness represented as the sum of the individual brightness values for each pixel. It also serves to convert the image data of each inspection area into a binary form by using the aforementioned binary threshold value, thereby extracting each of the R, G and B color patterns.

The inspection unit 17 receives the judgment reference value from the teaching table 18 and judges whether the position, size and shape of solder are correct or not by comparing characteristic quantities of the color patterns extracted by the image processor 15 with the judgment reference value, outputting the result of the judgment to the CPU 11. Upon collecting the results of such judgments for all inspection areas, the CPU 11 judges whether the target circuit board being inspected is defective or not. The result of this final judgment is outputted to the CRT display device 20 and the printer 21 or transmitted to the communication device 22.

The input device 19 is for the purpose of inputting various conditions for the inspection as well as inspection data and may include a keyboard and a mouse. The CRT display device 20 (hereinafter simply "display device") receives image data, the results of inspection and input data from the input device 19 and displays them on a display screen. The printer 21 serves to receive data such as the results of inspection from the CPU 11 and prints them out in a predetermined format.

The communication device 22 is for the purpose of exchanging data with other apparatus such as a device for mounting electronic components and a soldering device. When an inspected circuit board 1T is found to be defective, for example, its ID as well as data on its defects may be transmitted to a repairing device on the downstream side such that the defective portion may be repaired. The external memory device 23 is for writing and reading data on and from a memory medium such as a flexible disk and a photo-electromagnetic disk, and is used for storing results of inspection and receiving necessary programs and set data necessary for the inspection from outside.

Of the above, the image processor 15 and the inspection unit 17 may each be comprised of a dedicated processor having programs installed for carrying out the various processes described above. Instead, the CPU 11 for carrying out main controls may be additionally provided with the functions of the image processor 15 and the inspection unit 17.

According to one example of this invention, the R, G and B light sources 8, 9 and 10 are positioned such that the flat portion of the solder surface within the range of 5–15° in terms of the angle from the plane of the circuit board, the gently sloped surface portion within the range of 15–22.5° and the steeply sloped surface portion within the range of 22.5–37.5° will be detected respectively by the R, G and B light.

In this example, furthermore, a white-colored diffusive reflecting plate is used instead of a circuit board to adjust the quantities of light from the sources 8, 9 and 10 such that the beams of light therefrom are mixed together to produce a white color. This adjustment is carried out by obtaining an image by placing the aforementioned white diffusive reflecting plate with its reflecting surface disposed horizontally and adjusting the quantities of light from the sources 8, 9 and 10 such that the color of the diffusive reflecting surface on the image will become the same white as the original white color of the plate.

Figure 2:
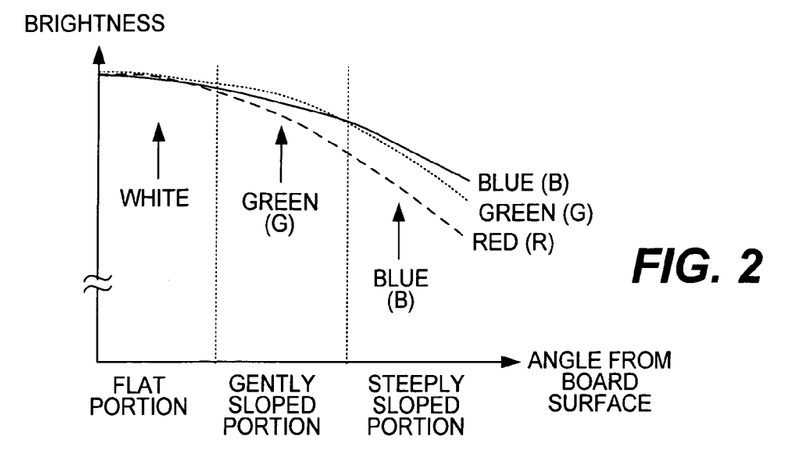
FIG. 2 is a graph of brightness characteristic obtained from an image of a diffusive reflecting surface after adjustment.

FIG. 2 shows the relationship between the brightness of R, G and B obtained when an image obtained of the diffusive reflecting plate illuminated from the sources 8, 9 and 10 after the aforementioned adjustment has been carried out and the sloping angle of the plate (measured from the surface of the circuit board).

Since the adjustment described above is normally carried out by setting the reflecting plate in the horizontal direction, the intensity of the R light at the angles corresponding to the flat portion of the solder surface becomes nearly the same as that of the G and B light. As a result, a white pattern will appear on the image, instead of a read pattern. In the gently sloped and steeply sloped portions, the color corresponding to the slope on the solder surface becomes slightly dominant and hence whitish green and blue patterns appear in these regions.

If lead-free solder is observed with an optical system thus set, the result is not as distinctive as explained above for the case of a diffusive plate but the differences in brightness among R, G and B become smaller on every sloped surface portion. Although the differences among the colors depend on the condition of unevenness on the solder surface, the white component on the image becomes large especially if the diffusive reflectivity is high, and a generally whitish image is obtained. At the time of teaching with a device of this type, a binary threshold value may be set by specifying a region on the screen with a coloring corresponding to each color pattern on the displayed image. If the image becomes too white, however, it becomes difficult to identify a region suitable for obtaining a binary threshold value and the efficacy of teaching becomes low. Another problem when the differences in brightness among the color components become small is that it is difficult to stabilize the accuracy of inspection.

When lead-free solder is inspected in this example, therefore, a process of adjusting the brightness of each color component by a value corresponding to the angle of slope ("the brightness-adjusting process") or a process of removing the white component resulting from the mixing of the color components ("the whiteness-removing process") is carried out. At the time of the teaching, an image adjusted by such a process is displayed for generating inspection data by setting a binary threshold value or a judgement reference value. At the time of an inspection, the image of the object to be inspected is similarly processed and the aforementioned binary threshold value or judgment reference value is applied on the image thus adjusted to determine whether the soldered part is defective or not.

These two adjustment processes are described next more in detail.

Figure 3:
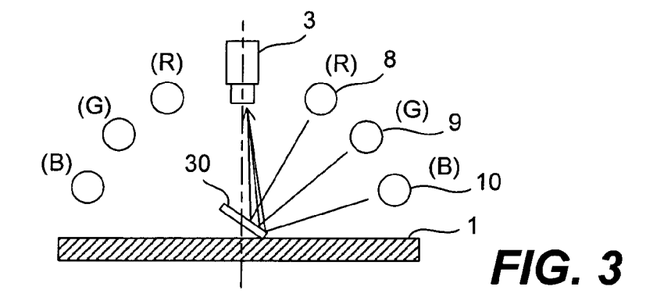
FIG. 3 is a schematic drawing for showing a method of determining multiplicative factors for the brightness-adjusting process.

In the brightness-adjusting process, the brightness of R, G and B light at each pixel is multiplied individually by a specified multiplicative factor in order to obtain an adjusted image. These multiplicative factors may be determined by obtaining images of a diffusive reflecting plate 30 by setting it at the sloping angles corresponding to the angular positions of the light sources 8, 9 and 10 sequentially, as shown in FIG. 3, and adjusting the brightness of the image obtained at each of the sloping angles. Alternatively, these factors may be determined by using an image of a soldered portion of a known shape and making adjustments such that each color pattern on this image will correspond to the shape of the solder.

Figure 4:
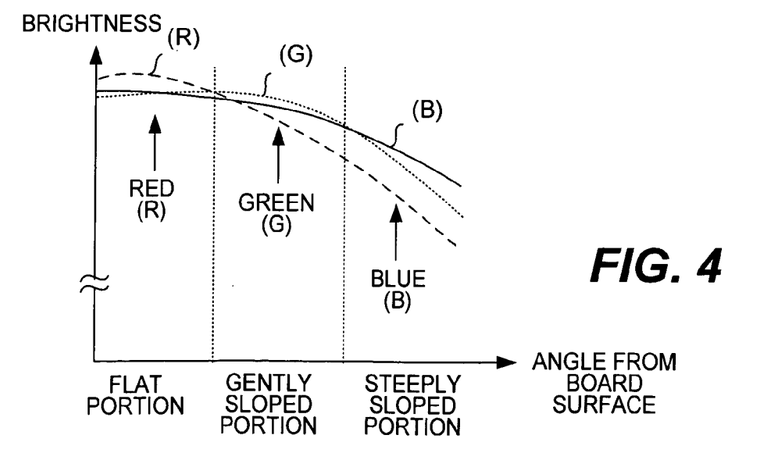
FIG. 4 is a graph of brightness characteristic obtained from an image of a diffusive reflecting surface after the brightness-adjusting process.

As an example, multiplicative factors for the three color components were selected by the method of using the diffusive reflecting plate 30 described above such that in each of the ranges of sloping angle (5–15°, 15–22.5° and 22.5–37.5°) the brightness of the color component to be dominant in that range will become greater than the brightness of the other color components. The factors thus obtained were 1.07 for R, 1.03 for G and 1.00 for B. FIG. 4 shows the brightness characteristics obtained with this diffusive reflecting plate 30 after this brightness-adjusting process has been carried out. It is to be noted that R is dominant within the range of angles corresponding to the flat surface portion, G is dominant within the range corresponding to the gently sloped surface portion and B is dominant in within the range corresponding to the steeply sloped surface portion.

Since these factors are necessary for maintaining the relationships among the angular positions of the light sources 8, 9 and 10 and the detection ranges of the colors, it is preferable to store them as long as the positional relationships among the light sources 8, 9 and 10 remain the same.

If the multiplicative factor for R alone were increased, for example, the range of angles within which R becomes dominant would become wider and a red pattern may begin to appear also in a part of the gently sloped surface portion. This will upset the relationships among the angular positions of the light sources and the ranges of detection.

The multiplicative factors thus determined may be stored in the memory device 13 such that whenever an image of a target area including lead-free solder is thereafter processed, or the brightness-adjusting process may be carried out whenever the operator so desires by using the stored factors on the inputted image data.

The whiteness-removing process is also carried out in units of pixels. In the present example, both a first process of eliminating the white component generated by mixing the three color components and a second process of adjusting the brightness so as to restore the original total brightness while maintaining the dominance relationships among the color components (the "brightness-restoring process") are sequentially carried out.

Figure 5:
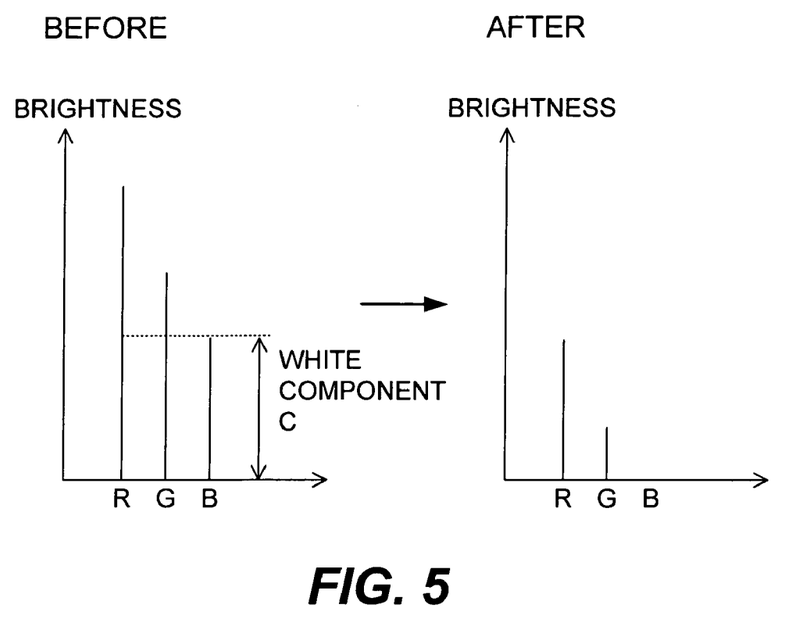
FIG. 5 is a drawing for showing an example of the whiteness-removing process.

FIG. 5 is referenced next to explain the principle of the whiteness-removing process.

One process of eliminating the white component is based on the premise that each of the color components R, G and B after the brightness adjustment is equal to the sum of the color component corresponding to the original mirror-reflected light and the white component due to the diffusive reflection of each color. Let $(R_{in}, G_{in}, B_{in})$ and $(R_m, G_m, B_m)$ represent the brightness of R, G and B before and after the white component is eliminated in the aforementioned whiteness-removing process. Let $(R_S, G_S, B_S)$ represent the brightness of mirror-reflected light, and let C represent the brightness of the white component contained in each of the color components. Then, we find:

$$(R_m, G_m, B_m) = (R_{in} - C, G_{in} - C, B_{in} - C)$$
$$= (((R_S + C) - C), ((G_S + C) - C), ((B_S + C) - C))$$
$$= (R_S, G_S, B_S).$$

This shows that the brightness gradation of each color component after the elimination of the white component turns out to be equal to that before the whiteness-removing process.

Since the white component is a mixture of the R, G and B components at equal proportions, it is desirable to eliminate as much as possible these mixed parts of the color components not corresponding to the angle of the sloped surface of the object being inspected. For this reason, the smallest brightness among the R, G and B components is extracted as the aforementioned white component C and this smallest brightness quantity is subtracted from each of the three color components. If use is made of the HSI conversion which is a representative method of calculating the hue, the hue $H_m$ represented by $(R_m, G_m, B_m)$ can be shown as below to be the same as the hue $H_{in}$ represented by $(R_{in}, G_{in}, B_{in})$:

$$H_m = (G_m - B_m)/(R_m + G_m - 2B_m)$$
$$= ((G_{in} - C) - (B_{in} - C))/((R_{in} - C) + (G_{in} - C) - 2(B_{in} - C))$$
$$= (G_{in} - B_{in})/(R_{in} + G_{in} - 2B_{in})$$
$$= H_{in}.$$

The aforementioned second process of adjusting the brightness to restore the original total brightness may be effected by noting that the total brightness before the removal of the white component in the whiteness-removing process is $L_{in}=(R_{in}+G_{in}+B_{in})$ and that after the removal is $(R_m+G_m+B_m)$. If the color components of the brightness-restored image are written as $(R_{out}, G_{out}, B_{out})$, the restoration of the original total intensity may be effected as follows:

$R_{out}=R_m(R_{in}+G_{in}+B_{in})/(R_m+G_m+B_m),$ $G_{out}=G_m(R_{in}+G_{in}+B_{in})/(R_m+G_m+B_m),$ and $B_{out}=B_m(R_{in}+G_{in}+B_{in})/(R_m+G_m+B_m).$ It can be shown easily that the total brightness of the brightness-restored image $L_{out}=(R_{out}+G_{out}+B_{out})$ is equal to $L_{in}$.

In this manner, the white component generated by the mixing of the different color components can be eliminated while maintaining the hue and brightness of the original image before the elimination of the white component. Thus, the R, G and B components can be made more clearly distinguishable.

Figure 6:
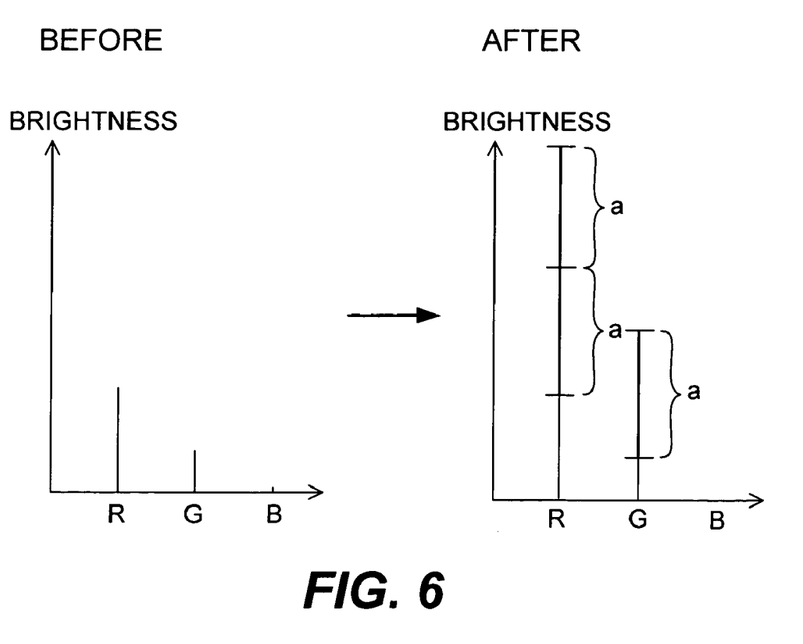
FIG. 6 is a drawing for showing an example of brightness-restoring process.

Although the brightness-restoring process described above is characterized in that the brightness of each color component is increased by the same multiplicative factor $(R_{in}+G_{in}+B_{in})/(R_m+G_m+B_m)$, the restoration to the original brightness $L_{in}$ may be effected in different manners. FIG. 6 shows another example wherein the brightest color component is identified after the white component is removed (R in the example of FIG. 6) and a specified quantity ("2a" in FIG. 6) of brightness is added to this color component while one half of this quantity ("a" in FIG. 6) of brightness is added to the next brightest color component (G in the example of FIG. 6). If this specified quantity of brightness is made equal to the aforementioned brightness C (representing the brightness of the white component in each color component), it can be shown as below that the original brightness is restored by the process described above:

$$L_{out} = R_{out} + G_{out} + B_{out}$$
$$= (R_m + 2C) + (G_m + C) + B_m$$
$$= R_m + G_m + B_m + 3C$$
$$= (R_{in} - C) + (G_{in} - C) + (B_{in} - C) + 3C$$
$$= R_{in} + G_{in} + B_{in}$$
$$= L_{in}.$$

Figure 7:
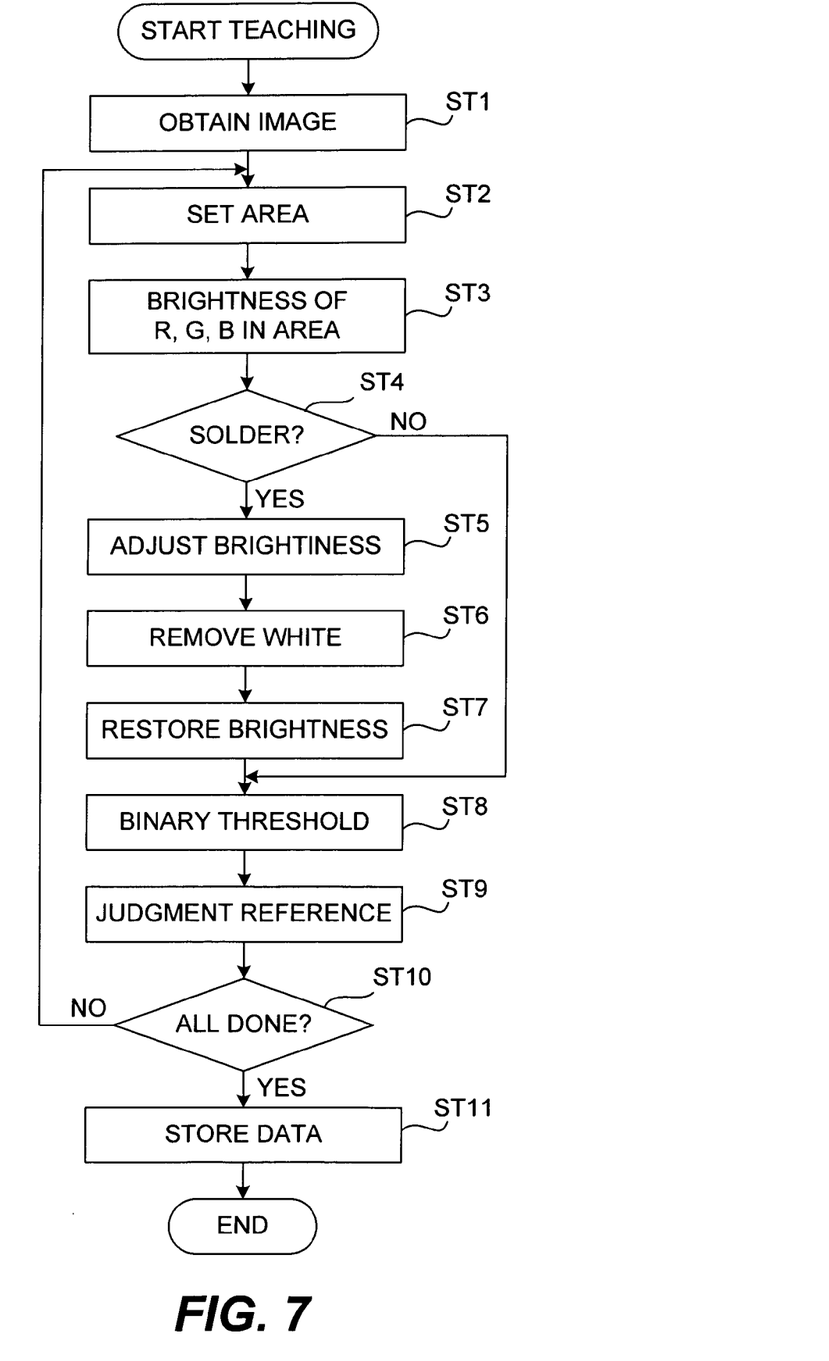
FIG. 7 is a flowchart for the teaching process.

FIG. 7 shows a teaching routine for the inspection device 17. To start, the operator operates the input device 19 to register data on the circuit board to be inspected such as its name and its size, sets the standard circuit board 1S on the Y-table 7 and obtains its image while illuminating it with the light projecting device 4 (Step ST1). After R, G and B image signals are thereby received by the image input device 12, they are converted into digital signals and variable-density color image data to be processed are inputted to the memory device 13. The inputted color image is displayed on the display device 20.

An image is obtained by positioning the image pick-up device 3 and the light projecting device 4 with respect to a specified target part to be inspected. The operator specifies a target area for inspection, say, by means of a mouse. In response, the CPU 11 temporarily stores the position and size data of the specified area to be inspected in the memory 13 (Step ST2). Next, R, G and B brightness is extracted for each pixel within the area to be inspected (Step ST3).

If the specified area to be inspected includes solder (YES in Step ST4), the operator inputs an enable-control data item indicative of this fact and the aforementioned brightness-adjusting, whiteness-removing and brightness-restoring processes are carried out (Steps ST5–ST7). Although not illustrated, the display on the display device 20 is replaced by that of the area to be inspected, showing the brightness after the final adjustment ($R_{out}, G_{out}, B_{out}$). The operator references this displayed image to input an optimum binary threshold value for extracting each color pattern for showing the soldered positions. This value is taken in by the CPU 11 and stored in the memory device 13 in correlation with the position and size data on the target area to be inspected (Step ST8). The area, shape and position of the solder are calculated from the color patterns extracted by using this binary threshold value and the reference value for the judgement processing is set on the basis of these calculated values (Step ST9).

Thereafter, images of the other inspection positions of the circuit board are taken, target areas for inspection are similarly set and the series of processes is carried out for setting a binary threshold value and a reference value. At inspection positions not including solder, the aforementioned enable-control data are not inputted (NO in Step ST4) and Steps ST5–ST7 are not carried out. The setting process is effected by directly using the inputted image.

If the aforementioned setting process is completed at all inspection positions (YES in Step ST10), a judgment data file is created from the inspection data for each inspection position temporarily stored in the memory device 13 and is stored in the teaching table 18 (Step ST11). Within this judgment data file, an enable-control flag is set at each area specified as a target area to be inspected.

Figure 8:
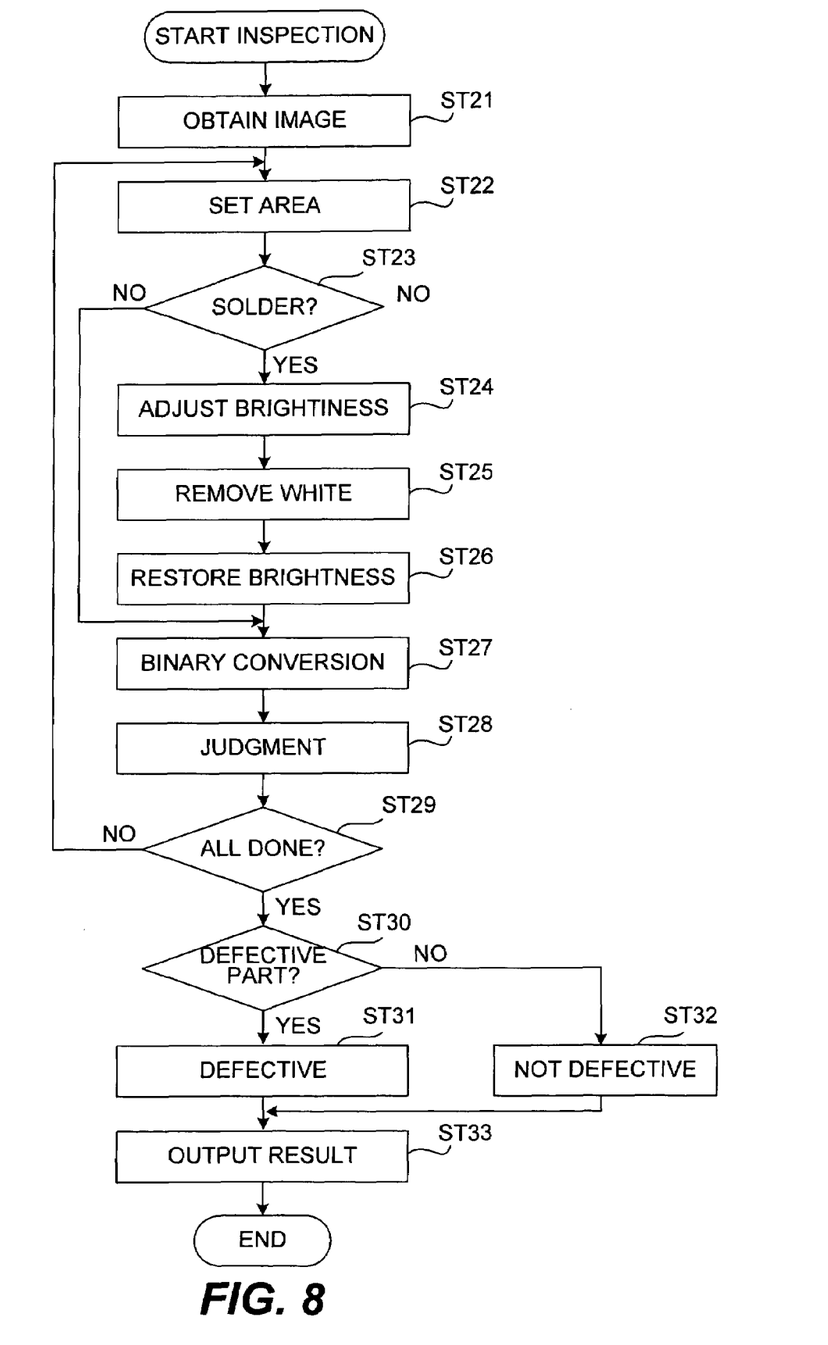
FIG. 8 is a flowchart for the inspection process.

FIG. 8 shows a routine for automatic inspection by the inspection unit 17 for each circuit board. In other words, this routine is to be repeated as many times as there are circuit boards to be inspected.

Before starting this routine, the operator specifies the type of the target circuit board 1T to be inspected, say, by inputting its name. In response, the CPU 11 retrieves from the teaching table 18 the judgment data file corresponding to this target circuit board 1T and sets it in the memory device 13. The inspection routine is started under this condition, the target circuit board 1T being transported onto the Y-table 7 and its image being taken (Step ST21).

Next, the CPU 11 positions the image pick-up device 3 and the light projecting device 4 with reference to the first inspection position on the basis of the set data in the judgment data file, creates its image and sets a target area of inspection of this image (Step ST22). If one of the aforementioned enable-control flags is set at this target area (YES in Step ST23), the brightness-adjusting, whiteness-removing and brightness-restoring processes are sequentially carried out (Steps ST24–26).

Thereafter, the aforementioned binary threshold value is used to extract R, G and B color patterns by converting the variable-density image of the target area in a binary form (Step ST27). Next, the extracted color patterns are used to calculate the area, shape and position of the solder and these results are compared with the judgment reference values to conclude whether or not the soldered part is defective or not (Step ST28).

Images are similarly taken of other inspection positions sequentially, based on the set data in the judgment data file, target areas are set, and a judgment is made whether or not this inspection position is defective or not on the basis of the image data within this target area. For target areas not including solder (NO in Step ST23), the processes of Steps ST24–ST26 are skipped, the inputted image is used directly for converting to a binary image, and the judgment process is carried out.

After all inspection positions have thus been inspected (YES in Step ST29), each target circuit board 1T which has been inspected is judged to be either defective or not on the basis of the results of judgment at each inspection position (Steps ST30–ST32). The result of judgment is outputted (Step ST33) and this inspection routine is concluded.

Thus, when a circuit with lead-free solder is inspected by an inspection device according to this invention, a brightness-adjusting process is carried out to adjust brightness of color components such that the color component corresponding to each of the flat, gently sloped and steeply sloped surface portions of the solder becomes dominant over the other color components. In addition, the white component is removed from each of the color components such that segments of the solder surface can be clearly represented distinctively by the R, G and B color components. Thus, the operator can easily determine an area from which an appropriate binary threshold value can be set and both the binary threshold value and the judgment reference value can be set efficiently. At the time of an inspection, the binary threshold value and the judgment reference value thus determined are used on an image which has been adjusted similarly such that a dependable inspection can be carried out in a stable manner.

What is claimed is:

1. A method of inspecting surface conditions of an object with a curved surface placed on a reference plane, said method comprising the steps of:
    obtaining an image from reflected light from said curved surface irradiated by a light including a plurality of color components having different colors projected from different directions with respect to said reference plane;
    carrying out, within an image area in the obtained image, an extracting process by extracting for each pixel the brightness of a white component generated by mixing all of said color components and a brightness-reducing process by reducing the brightness of each of said color components of each pixel by an amount corresponding to the extracted brightness of the white component of the pixel;
    carrying out, from each pixel of said image area for which said brightness-reducing process has been carried out, a brightness-restoring process by varying the brightness of each of said color components such that the brightest of said color components becomes more strongly emphasized compared to the others of said color components than before said brightness-reducing process and the loss in total brightness caused by said brightness-reducing process is restored; and
    carrying out an inspection of surface conditions of said curved surface based on a distribution of said color components in said image after said brightness-restoring process.

2. The method of claim 1 wherein said inspection is carried out by comparing distributions of said color components with a predetermined model data and thereby determining whether or not said surface conditions are good according to a predetermined standard.

3. The method of claim 1 wherein the step of carrying out said inspection includes the steps of displaying the image after said brightness-restoring process and inputting a data item indicative of a judgment result of an inspection by an operator based on the image of said curved surface displayed in said step of displaying.

4. A method of inspecting surface conditions of an object with a curved surface placed on a reference plane, said method comprising the steps of:
    obtaining a first image of a diffusive reflecting surface at a selected angle with respect to said reference plane under a condition of illumination by light consisting of a plurality of color components having different colors projected from different directions with respect to said reference plane;
    determining multiplicative factors by which brightness of each of said color components of said first image is individually adjusted such that the color component corresponding to light from an angle corresponding to said arbitrarily selected angle becomes brighter than the others of said color components;

obtaining a second image of reflected light from said curved surface under a same condition as said condition of illumination under which said first image of said diffusive reflecting surface was obtained;

carrying out an adjustment process by adjusting the brightness of each of said color components, within an area of said second image containing an image of said object, by said multiplicative factors;

carrying out a whiteness-extracting process by extracting, from each pixel of said area after said adjustment process, the brightness of the white component generated by mixing all of said different colors and a brightness-reducing process by reducing the brightness of said color components, for each said pixel, by an amount corresponding to the brightness of the white component extracted in said whiteness-extracting process;

carrying out, for each pixel of said area for which said brightness-reducing process has been carried out, a brightness-restoring process by varying the brightness of each color component such that the brightest of said color components becomes more strongly emphasized with respect to the others of said color components than before said brightness-reducing process and the loss in total brightness caused by said brightness-reducing process is restored; and carrying out an inspection of surface conditions of said curved surface based on a distribution of said color components in said image after said brightness-restoring process.

5. The method of claim 4 wherein said inspection is carried out by comparing distributions of said color components with a predetermined model data and thereby determining whether or not said surface conditions are good according to a predetermined standard.

6. The method of claim 4 wherein the step of carrying out said inspection includes the steps of displaying the image after said brightness-restoring process and inputting a data item indicative of a judgment result of an inspection by an operator based on the image of said curved surface displayed in said step of displaying.

7. A device for inspecting a printed circuit board, said device comprising:

a light projecting device having a plurality of light sources emitting light of different colors, arranged at different angles with respect to a reference surface;

an image pick-up device for generating an image from reflected light from said printed circuit board;

an image inputting device for receiving the image generated by said image pick-up device with each of said light sources lit;

whiteness-removing means for carrying out a whiteness-extracting process by extracting, from each pixel of an area of said image inputted by said image inputting device and containing an image of solder, the brightness of the white component generated by mixing all of said different colors and a brightness-reducing process by reducing the brightness of said color components, for each said pixel, by an amount corresponding to the brightness of the white component extracted in said whiteness-extracting process;

brightness-restoring means for carrying out, for each pixel of said area for which said brightness-reducing process has been carried out, a brightness-restoring process by varying the brightness of each color component such that the brightest of said color components becomes more emphasized with respect to the others of said color components than before said brightness-reducing process and the loss in total brightness caused by said brightness-reducing process is restored;

judging means for judging surface conditions of said solder by comparing preliminarily set model data with distribution of each of said colors in said area within said image after said brightness-restoring process; and an output device for outputting results of judgment by said judging means.

8. The device of claim 7 further comprising a brightness-adjusting means for carrying out a brightness-adjusting process by adjusting the brightness of each of said color components, within an area containing an image of said solder, by using predetermined multiplicative factors, wherein said whiteness-removing means carries out said whiteness-removing process on an image obtained by said brightness-adjusting process by said brightness-adjusting means.

9. The device of claim 8 wherein said multiplicative factors are determined for each of said color components such that, when a reference image of a diffusive reflecting surface at an arbitrary angle with respect to said reference surface is obtained by said image pick-up device while each of said light sources is lit, the color component corresponding to the light at the angle corresponding to the said arbitrary angle becomes brighter than the others of said color components.

10. A device for inspecting a printed circuit board, said device comprising:

a light projecting device having a plurality of light sources emitting light of different colors, arranged at different angles with respect to a reference surface;

an image pick-up device for generating an image from reflected light from said printed circuit board;

an image inputting device for receiving the image generated by said image pick-up device with each of said light sources lit;

whiteness-removing means for carrying out a whiteness-extracting process by extracting, from each pixel of an area of said image inputted by said image inputting device and containing an image of solder, the brightness of the white component generated by mixing all of said different colors and a brightness-reducing process by reducing the brightness of said color components, for each said pixel, by an amount corresponding to the brightness of the white component extracted in said whiteness-extracting process;

brightness-restoring means for carrying out, for each pixel of said area for which said brightness-reducing process has been carried out, a brightness-restoring process by varying the brightness of each color component such that the brightest of said color components becomes more emphasized with respect to the others of said color components than before said brightness-reducing process and the loss in total brightness caused by said brightness-reducing process is restored;

a display device for displaying an image after said brightness-restoring process; and an input device for allowing a user to input an data item indicative of a judgment result of an inspection based on the image of said solder displayed on said display device.

11. The device of claim 10 further comprising a brightness-adjusting means for carrying out a brightness-adjusting process by adjusting the brightness of each of said color components, within an area containing an image of said solder, by using predetermined multiplicative factors, wherein said whiteness-removing means carries out said whiteness-removing process on an image obtained by said brightness-adjusting process by said brightness-adjusting means.

12. The device of claim 11 wherein said multiplicative factors are determined for each of said color components such that, when a reference image of a diffusive reflecting surface at an arbitrary angle with respect to said reference surface is obtained by said image pick-up device while each of said light sources is lit, the color component corresponding to the light at the angle corresponding to the said arbitrary angle becomes brighter than the others of said color components.

* * * * *